United States Patent [19]

Jommi et al.

[11] Patent Number: 4,743,700

[45] Date of Patent: May 10, 1988

[54] PROCESS FOR FLUORINATING 1-PHENYL-2-AMINO-1,3-PROPANEDIOL COMPOUNDS

[75] Inventors: Giancarlo Jommi, Milan; Dario Chiarino, Monza; Roberto Pagliarin, San Giorgio Su Legnano, all of Italy

[73] Assignee: Zambon S.p.A., Vicenza, Italy

[21] Appl. No.: 697,568

[22] Filed: Feb. 1, 1985

[30] Foreign Application Priority Data

Feb. 3, 1984 [IT] Italy ................... 19435 A/84

[51] Int. Cl.$^4$ ................... C07D 263/04; C07D 103/40
[52] U.S. Cl. ................... 548/216; 546/270; 546/275; 548/217; 548/222; 548/224; 548/229; 548/237; 548/239; 564/86; 564/211
[58] Field of Search ............ 548/216, 217, 222, 224, 548/229, 228, 237, 239; 546/270, 275

[56] References Cited

U.S. PATENT DOCUMENTS 4,235,892 11/1980 Nagabhushan ............ 564/212

OTHER PUBLICATIONS

Jommi et al., Chem. Abst. 103-22574n.

Milos Hudlicky, Chemistry of Organic Flurine Compounds, pp. 112–113.
Chemistry and Industry, Feb. 8, 1958, p. 157–Ref. 87 (A) J.A.C.S., 77, 4899, (1955) "Synthesis of Alkyl and Substituted Alkyl Fluorides from p-Toluenesfulfonic Acid Esters, the Preparation of p-Toluenesulfonic Acid Esters of Lower Alcohols by Walter F. Edgell and L. Parts–Ref. 23 (B).
Can. J. Chem., 34, (1956) "The Preparation and Some Cleavage Reactions of Alkyl and Substituted Alkyl Methanesulphonates by F. L. M. Pattison and J. E. Millington Ref. 820 (C).
10–Organic Chemistry p. 6154–Ref. 869 (D).

*Primary Examiner*—Donald G. Daus
*Assistant Examiner*—Cecilia Shen
*Attorney, Agent, or Firm*—Cushman, Darby & Cushman

[57] ABSTRACT

Replacement with fluorine of the primary hydroxy group of 1-phenyl-2-amino-1,3-propanediol compounds wherein the secondary hydroxy group and the amino group have been suitably protected.

The reaction is carried out with an inorganic fluoride in a polyglycol.

New oxazoline compounds particularly useful in said process.

9 Claims, No Drawings

PROCESS FOR FLUORINATING 1-PHENYL-2-AMINO-1,3-PROPANEDIOL COMPOUNDS

This invention relates to a new process for replacing the primary hydroxy group of 1-phenyl-2-amino-1,3-propanediol compounds with fluorine and to new intermediates useful in said process.

More particularly, this process relates to a very important step in the preparation of the Compounds of Formula:

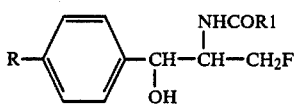 (I)

wherein:

R is —NO$_2$, CH$_3$S—, CH$_3$SO—, or CH$_3$SO$_2$—; and
R1 is mono-, di-, or tri-halomethyl.

The Compounds of Formula I have two asymmetric carbon atoms and can exist as stereoisomers. Unless otherwise specified herein or in the claims, it is intended to include all four stereoisomers, whether separated or mixtures thereof. D-(threo)-forms are preferred because of their broader antibacterial activity.

U.S. Pat. No. 4,235,892 discloses the Compounds of Formula I and a process for their preparation. This process essentially consists in N-protecting a 1-(phenyl)-2-amino-1,3-propanediol (the phenyl moiety of which is variously substituted) by an imido derivative of a dicarboxylic acid, in treating the thus obtained compound with dialkylaminosulfotrifluoride (DAST), in removing the N-protective group and then in acylating the thus obtained 1-(phenyl)-1-hydroxy-2-amino-3-fluoro-propane with the desired haloacetic acid or with a suitable reactive derivative thereof.

Although apparently easy, this process suffers many disadvantages and affords low yields.

One of the main disadvantages is that the replacement of the primary hydroxy group by fluorine is not selective and leads to the formation of many by-products among which may be mentioned, for instance, the products deriving from the substitution of the secondary hydroxy group. The desired compound may thus be obtained at a sufficient purity degree only by a particularly complex column chromatography process. Another disadvantage is that DAST is the only agent which allows to perform the fluorination step on the peculiar intermediate products which are prepared according to the process of U.S. Pat. No. 4,235,892 and DAST is very expensive and dangerous, especially when it is intended for large scale production.

It has been now found a new process which overcomes the above mentioned disadvantages. Essentially, it consists in treating with the fluoride anion and in the presence of a polyglycol a 1-phenyl-2-amino--1,3-propanediol compound (substituted on the phenyl ring) wherein have been contemporaneously protected the hydrogen atom of the secondary hydroxy group and at least one hydrogen atom of the primary amino group) and wherein the hydrogen atom of the primary hydroxy group has been replaced by a leaving group which activates the substitution with fluorine.

1-Phenyl-2-amino-1,3-propanediol compounds which meet with these requirements may be represented by the following formula

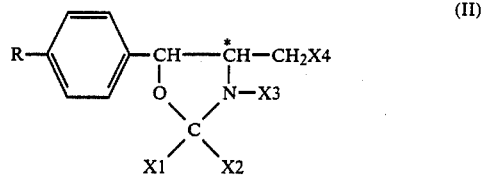 (II)

where

R is a methylthio, methylsulfoxy, methylsulfonyl or a nitro group; and

X1 is hydrogen, 1–6C alkyl, 1–6C haloalkyl, 3–6C cycloalkyl, phenyl or phenylalkyl(1–6C), where the phenyl ring may be substituted by one or two halogen, 1–3C alkyl, 1–3C alkoxy or nitro groups; or X1 together with X2 is an oxygen atom or an alkylene having from two to five carbon atoms; or X1 together with X2 and R4 is a chain of formula

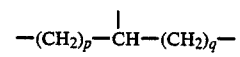

where p is 3 or 4 and q is 1 or 2; and

X2 is hydrogen, 1–6C alkyl, 1–6C haloalkyl, 3–6C cycloalkyl or phenyl which may be substituted by one or two halogen, 1–3C alkyl, 1–3C alkoxy or nitro groups; or X2 together with X1 has the above mentioned meanings; or X2 together with X3 is a covalent bond; or X2 together with R4 is

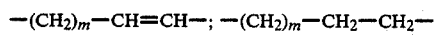

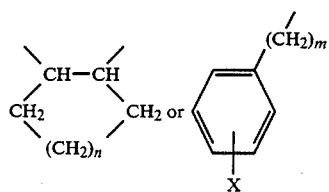

where n is 1 or 2; m is 0 or 1; X is hydrogen, halogen, 1–3C alkyl, 1–3C alkoxy or nitro; or X2 together with X1 and R4 has the above mentioned meanings; and X3 is hydrogen or —CO—R4 where R4 is hydrogen, 1–6 alkyl, 1–6C haloalkyl, 3–6C cycloalkyl, phenyl or phenylalkyl(1–6C), where the phenyl ring may be substituted by one or two halogen, 1–3C alkyl, 1–3C alkoxy or nitro groups; or R4 together with X2 has the above mentioned meanings; or R4 together with X2 and X1 has the above mentioned meanings; or X3 together with X2 has the above mentioned meanings; and X4 is —O—SO$_2$R6 where R6 is methyl, trifluoromethyl, phenyl, p-methyl-phenyl, 2,4,6-trimehylphenyl, 2-naphthyl or 2-pyridyl.

A preferred embodiment of this invention contemplates the use of a Compound of Formula II where R and X4 have the above mentioned meanings; and X2 together with X3 is a covalent bond; and X1 is hydrogen, 1-6C alkyl, 1-6C haloalkyl, 3-6C cycloalkyl, phenyl or phenyl-(1-6C)alkyl wherein the phenyl ring may be substituted with one or two halogen, 1-3C alkyl, 1-3C alkoxy or nitro groups.

These Compounds are referred hereinafter as Compounds IIa.

The replacement of the group X4 with fluorine is a complex technical problem particularly when it is desired to use the most economical and amenable fluorination agents, that is the alkali and alkaline-earth metal fluorides, because F anion behaves besides as a nucleophilic agent also as a base causing competitive side-reactions such as elimination, hydrolysis or, whenever it is possible, solvolysis (E. V. & S. M. Dehmlow "Phase transfer catalysis" Verlag Chemie, 1980, page 80).

Because of the peculiar nature of the hydrogen atom that is marked with an asterisk in Formula (II), the Compounds (II) undergo elimination. When they have been reacted with F$^-$ in phase transfer conditions or in the presence of crown ethers, they did not react or did afford low yields of the desired compound owing to the concomitant formation of hydrolization and elimination products.

Now, it has been found that these drawbacks can be overcome by the process of this invention.

The process of this invention is preferably carried out by reacting one mole of the Compound of Formula (II) with 1-15 moles of an inorganic fluoride in a polyglycol at a temperature of from 40° C. to 150° C. for 2-60 hrs.

Suitable inorganic fluorides are those which cause a reaction of nucleophilic type such as for instance the fluorides of alkali and alkaline-earth metals, of ammonium and phosphonium.

Preferred fluorides are sodium and potassium fluoride.

Suitable polyglycols are those whose viscosity at room temperature and at high temperatures is consistent with that kind of treatments which undergo the reaction mixture and have formula HO—(AO)$_s$—H, where A is a straight or branched alkylidene having 2-6 carbon atoms and s is an integer number ranging from 4 to 50. Preferably, there are used polyglycols whose molar weight ranges from 200 to 2000. Most preferably it is used polyethylene glycol 400.

The polyglycol can be used in admixture with other protic, aprotic or polar-aprotic organic diluents such as dimethylsulfoxide, dimethylformamide and diethyleneglycol-dimethylether.

The fluorination step affords the compounds of formula

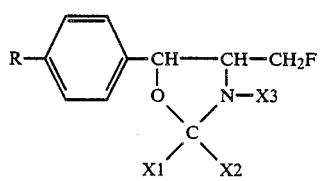

(III)

wherein X1, X2, X3 and R have the above mentioned meanings.

The Compounds of Formula (III) are then isolated by means of usual techniques. Also the removal of the protective groups and the subsequent treatment with the desired halo-acetic acid or with a reactive derivative thereof to afford the Compounds of Formula (I) are carried out according to usual techniques.

Some of the intermediate compounds useful in the process of this invention are new and they are a further object of this invention.

More particularly are new the Compounds of Formula:

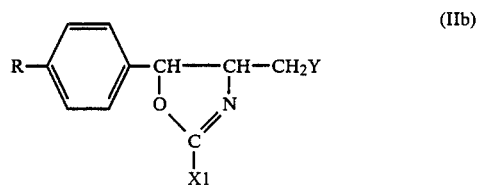

(IIb)

where

Y is F, OH or X4; and

R, X1, and X4 have the meanings mentioned above in connection with the compounds IIa provided, however, that Y is not OH when R is a nitro group.

Excepting when Y is F, the oxazolines of formula (IIb) are prepared according to known techniques (E. H. Rodd "Chemistry of carbon compounds" vol. IV°, Heterocyclic Compounds pag. 361 Elsevier Publishing Co. 1957; R. C. Elderfield "Heterocyclic compounds" Vol. V, J. Willey and Sons, Inc, pag. 377, 1957; Angew. Chem. Int. Ed. 15, 270-281, 1976, Chem. Rev. 71, 483-506, 1971, Chem. Rev. 44, 447-476, 1941) such as for instance the treatment of a suitable 1-phenyl-2-amino-1,3-propanediol (substituted at the phenyl ring) with an amidine of formula X1—C(=NH)—NH$_2$ or a salt thereof;

a halohydrate of an iminoether of formula X1—C-(OR')=NH$_2^+$X$^-$ an orthoester of formula X1—(OR')$_3$;

a nitrile of formula X1—CN;

wherein X1 has the meanings mentioned above in connection with formula IIa and R' is preferably an alkyl having low molecular weight.

Alternatively, they are prepared by dehydration (acidic catalysis) of an amide of formula

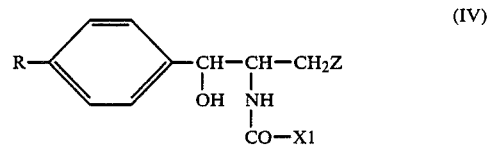

(IV)

or by cyclization (basic catalysis) of an active ester of formula

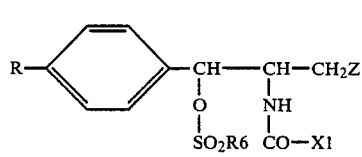

(V)

wherein

Z is OH or X4; and

X4, R and R6 have the above mentioned meanings; and

X1 has the meanings mentioned above in connection with formula IIa.

When Z is OH, the thus obtained oxazolines are esterified with a suitable sulfonic acid or a reactive derivative thereof, according to known techniques to afford the Compounds of Formula IIa.

Also the other Compounds of Formula II are prepared very easily by making use of cheap reactants.

When X1, X2 and R4, equal or different among them, are hydrogen, 1–6C alkyl, 1–6C haloalkyl, 3–6C cycloalkyl, phenyl or substituted phenyl, examples of suitable reactants are: aldehydes such as formaldehyde, acetaldehyde, valeraldehyde, caproaldehyde, benzaldehyde, anisaldehyde, 4-chlorobenzaldehyde, 4-ethoxy-3-methoxy-benzaldehyde, 2,6-dinitrobenzaldehyde or ketones such as acetone diethylketone or hexylmethylketone for protecting the secondary hydroxy group and one hydrogen of the amino group, and acids such as acetic, dichloroacetic, trifluoroacetic, pivaloyl, benzoic, 2,4-dibromobenzoic, veratric, 2,5-dimethylbenzoic or 4-nitrobenzoic acid, for protecting the second hydrogen of the amino group.

When X1 and X2, together, are an alkylene radical having from 2 to 5 carbon atoms, examples of suitable reactants are the cycloalkanones such as cyclopropanone, cyclopentanone or cyclohexanone.

When X1 together with X2 and R4 is a chain of formula

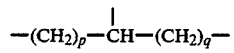

where p and q have the above mentioned meanings, examples of suitable reactants are the ketoacids such as (2-oxocyclopentyl)acetic acid, (2-oxocyclohexyl)-acetic acid, 3-(2-oxocyclopentyl)propionic acid and 3-(2-oxocyclohexyl)-propionic acid.

When X2 together with R4 forms a mono- or a polycylic system, examples of suitable reactants are the aldehydo-acids or the keto-acids such as phthalaldehydic acid, succinic semialdehyde, levulinic acid, 4-phenyl-4-oxo-butyric acid; hexahydrophthalaldehydic acid; (2-acetyl)-cyclohexylcarboxylic acid and (2-acetyl)-cyclopentyl-carboxylic acid.

When X1 together with X2 is an oxygen atom, examples of suitable reactants are the halocarbonates of formula XCOOR2 where X is a halogen atom and R2 is an alkyl, aralkyl or an aryl radical; preferably R2 is an 1–4C alkyl radical.

The preparation of Compounds II where X1 and X2, together, are an oxygen atom is based on the finding that Compounds of Formula

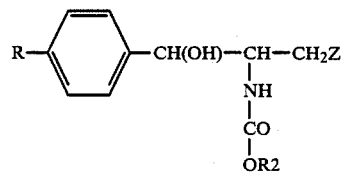

(VI)

where R, Z and R2 have the above mentioned meanings, cyclize regioselectively on the secondary hydroxy group to afford oxazolidinones of Formula II, in the presence of strong bases and of aprotic solvents.

The role of the solvent is critical. When the reaction is carried out in the presence of a non-aprotic solvent, the cyclization proceeds either on the secondary or on the primary hydroxy group and affords a mixture of the two possible cyclic compounds.

Examples of suitable aprotic solvents are the aromatic hydrocarbons such as benzene and toluene. Examples of suitable strong bases are the alkali and the alkaline earth metal alcoholates as well as the tertiary amines.

The cyclization reaction may also proceed via the intermediate formation of the alcoholate at the secondary hydroxy group when there are used alkali and alkaline earth metal alcoholates, alkali metal hydrides such as sodium hydride, sodium amide, Grignard-like organo-metallic derivatives and alkyl-lithium derivatives.

In turn the Compounds (VI) can be prepared according to known techniques such as the reaction of the desired 1-(phenyl)-2-amino-1,3-propanediol, substituted at the phenyl ring, with a compound of formula X—COOR2, where X is halogen and R2 has the above mentioned meanings, in the presence of a base and of a suitable diluent.

When it is used an organic diluent such as acetonitrile it is preferably used an organic base such as a tertiary amine, whereas is preferably used an inorganic base such as an alkali metal carbonate or bicarbonate when the reaction is carried out in aqueous medium. Alternatively it may be used a basic diluent such as pyridine.

The Compounds of Formula VI wherein R is —SCH3 are more soluble into the aprotic solvents than those wherein R is —SO—CH3 or SO2CH3. A preferred way for preparing Compounds (II) wherein R is —SO—CH3 or —SO2—CH3 comprises the preparation of the corresponding Compounds (VI) wherein R is —S—CH3, their subsequent cyclization and, lastly, their oxidation according to known techniques.

The substitution of the hydrogen of the primary hydroxy group with a —SO2R6 radical, where R6 has the above mentioned meanings, can be carried out prior to or after having protected both the secondary hydroxy and amino groups. Also this substitution can be carried out according to known techniques.

After perfomance of the fluorination step, the protective groups are removed from the Compounds of Formula II wherein X4 has been replaced by fluorine.

A preferred method is consisting in removing the protective groups with acids, preferably inorganic acids, in aqueous medium or in water/organic diluents mixtures. The latter media are preferred when hydrolysis regenerates the compound or the compounds which had been previously used as protective agents and when the amine which is formed is soluble in an aqueous solution of inorganic acids. It is thus obtained a repartion of the amine in the aqueous layer and of the protective agent or agents from which they are recovered and then recycled; in turn, the amine is recovered by precipitation via neutralization of the aqueous layer. Alternatively the amine can be extracted with a suitable organic solvent.

When X1 and X2, together are an oxygen atom, the protective group may also be removed through treatment with an organo-metallic derivative such as a Grignard's derivative and the subsequent hydrolysis in mild conditions with inorganic acids in water or in water/organic solvent mixtures.

Another possible method for removing the protective group when X1 and X2, together, are an oxygen atom, comprises the reduction of the keto group and the subsequent hydrolysis in mild conditions as described above. This reduction is preferably carried out with complex hydrides such as sodium borohydride.

After removal of the protective groups it is obtained a Compound of Formula

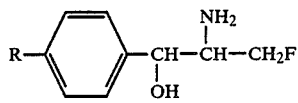   (VII)

which can be reacted with a haloacetic acid of Formula R1COOH, wherein R1 has the above mentioned meanings, or a reactive derivatives thereof to afford the desired compound of Formula (I).

This invention is illustrated by the following examples which should not be constructed as limiting it in any way.

EXAMPLE 1

Preparation of D-(threo)-3-acetoxy-1-(4-methylsulfonyl-phenyl)-2-phthalimido-1-hydroxy-propane (A)

D-(threo)-1-(4-methylsulfonylphenyl)-2-phthalimido-1,3-propanediol (1 g; 2.66 mmols), prepared as described in U.S. Pat. No. 4,235,892, has been dissolved in anhydrous pyridine (5 ml). Acetylchloride (0.2 ml; 2.83 mmols) has been added dropwise to this solution kept under stirring at 0° C.; after completion of the addition, the reaction mixture has been heated to 25° C. and kept under stirring for 1 hour; afterwards, the reaction mixture has been poured into water and ice, acidified with hydrochloric acid and extracted with ethyl acetate.

The crude product (A) has been obtained (quantitative yield) from the organic layer after drying over sodium sulfate and evaporation of the solvent in vacuo; the crude, after crystallization from methanol, gave a pure product (0.84 g; yield 75%) as shown by HPLC and TLC analysis:

Elemental Analysis for $C_{20}H_{19}O_9N$: (found): C 57.3%; H 4.6%; N 3.3%; (Calculated): C 57.55%; H 4.56%; N 3.36%.

The acetylation is regio-selective on the secondary hydroxy group as shown by NMR spectrum in DMSO; delta=1.78; s, 3H, $CH_3CO$—; 4.50 dd—2H, —$CH_2OAc$; 6.02, d, 1H, benzylic OH.

The following compounds can be prepared in a similar manner:
D- and L-(threo)-3-acetoxy-1-(4-methylthio-phenyl)-2-phthalimido-1-hydroxy-propane,
D- and L-(threo)-3-acetoxy-1-(4-nitrophenyl)-2-phthalimido-1-hydroxy-propane.

EXAMPLE 2

Reduction of compound (A) to 3-acetoxy-1-(4-methylsulfonyl)phenyl)-1-hydroxy-2-(3-hydroxy-1H-isoindol-1-one-2-yl)-propane (B).

Compound (A) (0.76 g; 1.82 mmols) has been added to a mixture of tetrahydrofuran and water (1:1; 4 ml); to this suspension, kept at 0° C. under vigorous stirring, has been added portionwise sodium borohydride (138 mg; 3.64 mmols).

As the reaction proceeded, the suspension became a homogeneous solution, after 1 hour and after having checked by TLC the disappearance of compound (A) and the formation of a new product, tetrahydrofuran has been evaporated in vacuo and the product extracted with ethyl acetate.

After drying over sodium sulfate and evaporation of the solvent, compound (B) (0.7 g; yield 92%) has been obtained sufficiently pure to undergo as such the following reaction (Example 3).

Compound (B) proved to be a mixture of two diasteroisomers because of the formation, during the reduction step, of a new asymmetric carbon atom; this has been proved by TLC, HPLC and NMR spectra in DMSO containing $D_2O$; delta 1.78; s, and 1.86, s, 3H on the whole, $CH_3$—CO in two diastereoisomers in the ratio 35:65; 5.84, s, and 6.24, s, 1H, on the whole

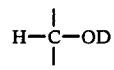

of the isoindole system (doublets, before deuteration, coupled with two doublets exhibiting delta=6.8 and 6.57 respectively, 1H on the whole for —OH in the two diastereoisomers) and, finally, 5.14, d, and 5.2, d, 1H on the whole for the two

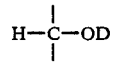

in position 1 of the propane chain.

The following compounds can be prepared in a similar manner:
3-acetoxy-1-(4-methylthio-phenyl)-1-hydroxy-2-(3-hydroxy-1H-isoindol-1-one-2-yl)-propane,
3-acetoxy-1-(4-nitro-phenyl)-1-hydroxy-2-(3-hydroxy-1H-isoindol-1-one-2-yl)-propane.

EXAMPLE 3

Cyclization of compound (B) to 3-acetoxymethyl-2-(4-methylsulfonyl-phenyl)-2,3-dihydro-oxazole-[2,3,a]-isoindol-5(9bH)-one (C).

Product (B) (0.55 g; 1.3 mmol) has been suspended in benzene (5 ml) containing a little amount of p-toluensulfonic acid (5 mg); by heating, the mixture became a clear solution. A short time later the water formed during the reaction has been distilled azeotropically until water was absent in the distilled benzene and TLC analysis showed the disappearance of product (B). At the end, almost all benzene has been evaporated in vacuo; after having added some water, product (C) has been extracted with ethyl acetate. Crude product (C) has been obtained in quantitative yield from the organic phase after drying over sodium sulfate and evaporation of the solvent in vacuo.

Crude product (C) has been used as such for the subsequent hydrolysis (Example 4). An aliquot has been purified by chromatography on silica gel using ethyl acetate/petroleum ether in various ratios or pure ethyl acetate as eluents. It has been proved that the crude contained small amounts of some unidentified impurities; after purification by chromatography has been proved to be a mixture of two diasteroisomers as shown by TLC and HPLC analysis as well as by NMR spectrum in DMSO: delta 6.38, s, and 6.07 s, 1H on the whole,

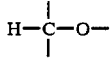

of the isoindole system; 2.08 s and 2.18 s, 3H on the whole, $CH_3CO-$; 3.19, s and 3.24, s, 3H on the whole, $CH_3SO_2-$.

Elemental analysis for $C_{20}H_{19}O_8N$: (calculated): C, 59.85%; H, 4.74%; N, 3.49%; (found): C, 59.9%; H, 4.6%; N, 3.6%.

The following compounds can be prepared in a similar manner:

3-acetoxymethyl-2-(4-methylthio-phenyl)-2,3-dihydro-oxazole[2,3a]-isoindol-5(9bH)-one, 3-acetoxymethyl-2-(4-nitro-phenyl)-2,3-dihydro-oxazole[2,3a]-isoindol-5(9bH)-one.

EXAMPLE 4

Hydrolysis of compound (C) to 2-(4-methylsulfonyl-phenyl)-3-hydroxymethyl-2,3-dihydro-oxazole-[2,3,a]-isoindol-5(9bH)-one (D)

Product (C) (0.2 g; 0.5 mmols) has been dissolved in methanol (2 ml) containing potassium hydroxide (42 mg; 0.75 mmols) at 0° C. and under vigorous stirring. After 30' the hydrolysis has been checked by TLC and showed the disappearance of product (C).

Methanol has been evaporated in vacuo and in the cold; the residue has been treated with water and extracted with ethyl acetate. The organic layer has been dried and evaporated to afford product (D) which has been recrystallized from ethyl acetate (0.16 g; yield 89%). The presence of two diastereoisomers in product (D) has been shown by NMR spectrum in DMSO, delta=6.3, s and 5.82, s, 1H on the whole,

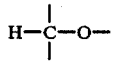

of the isoindole system; 3.18, s, and 3.22, s, 3H on the whole, $CH_3SO_2-$.

The following compounds can be prepared in a similar manner 2-(4-methylthio-phenyl)-3-hydroxymethyl-2,3-dihydro-oxazole[2,3a]-isoindol-5-(9bH)-one, 2-(4-nitro-phenyl)-3-hydroxymethyl-2,3-dihydro-oxazole-[2,3,a]-isoindol-5-(9bH)-one.

EXAMPLE 5

Preparation of 2-(4-methylsulfonyl-phenyl)-3-methanesulfonyloxymethyl-2,3-dihydro-oxazole[2,3,a]-isoindol-5-(9bH)-one (E)

Freshly distilled methanesulfonyl chloride (0.35 ml; 4.59 mmols) has been added to a solution of compound (D) (1.5 g; 4.17 mmols) in pyridine (3 ml), kept at 0° C. and under stirring. The mixture was allowed to stand in refrigerator overnight and then added with ice and extracted with ethyl acetate. The combined organic extracts has been dried over sodium sulfate and the solvent removed by evaporation.

Compound (E) has been thus obtained.

The following compounds can be prepared in a similar manner 2-(4-methylsulfonyl-phenyl)-3-trifluoromethanesulfonyloxymethyl-2,3-dhydro-oxazole[2,3a]-isoindol-5-(9bH)-one, 2-(4-methylsulfonyl-phenyl)-3-phenylsulfonyloxymethyl-2,3-dihydro-oxazole[2,3a]-isoindol-5-(9bH)-one, 2-(4-methylthio-phenyl)-3-4-methylphenyl)-sulfonyloxymethyl-2,3-dihydro-oxazole[2,3a]-isoindol h-5-(9bH)-one, 2-(4-nitro-phenyl)-3-(2,4,6-trimethylphenyl)-sulfonyloxymethyl-2,3-dihydro-oxazole[2,3a]-isoindol-5-(9bH)-one, 2-(4-methylsulfonyl-phenyl)-3-(2-naphthyl)-sulfonyloxymethyl-2,3-dihydro-oxazole[2,3a]-isoindol-5-(9bH)-one.

When treated according to the techniques described in Examples 15 and 18, these compounds afford the corresponding 3-F derivatives which are then suspended in 2N hydrochloric acid and refluxed for about 5–9 hours.

After cooling, the phthalaldehyide acid formed during the hydrolysis step is extracted with ethyl ether.

The aqueous layer is satured with sodium chloride and potassium carbonate, extracted with ethyl acetate and then with chloroform.

The combined organic extracts are dried over sodium sulfate and evaporated in vacuo to give the corresponding compounds of Formula VII which, without further purification, are boiled with the desired haloacetic acid in the presence of catalytic amounts of triethylamine to afford D-(threo)-1-(4-methylsulfonylphenyl)-1-hydroxy-2-dichloroacetamido-3-fluoro-propane, D-threo-1-(4-methylthio-phenyl)-1-hydroxy-2-trichloroacetamido-3-fluoro-propane, D-threo-1-(4-methylthio-phenyl)-1-hydroxy-2-trifluoroacetamido-3-fluoro-propane, D-threo-1-(4-nitro-phenyl)-1-hydroxy-2-dichloroacetamido-3-fluoro-propane.

EXAMPLE 6

Preparation of 1,3-dihydroxy-1-(4-methylthio-phenyl)-2-ethoxycarbonylamino-propane (F)

D-(threo)-1-(4-methylthio)-phenyl-2-amino-1,3-propanediol (1.06 g; 4.93 mmols) has been suspended into an aqueous solution of potassium carbonate (1.8 g of potassium carbonate into 20 ml of water) and the thus obtained mixture has been cooled, under vigorous stirring, to 0° C.

Ethyl chlorocarbonate (0.5 ml) has been dropped quickly into the mixture maintained under vigorous stirring at 0° C.; after half a hour, further 0.24 ml of ethyl chlorocarbonate (total amount: 7.74 mmols) has been added and the mixture has been maintained under stirring for 1 further hour.

At first the reaction mixture became clear and then a white precipitate has been slowly formed. After having checked the completion of the reaction by TLC, the suspension has been extracted with ethyl acetate. After drying on sodium sulfate, filtration and evaporation of the solvent, the organic extracts afforded 1.37 g of crude (H) (yield, 95.5%) which has been recrystallized from ethyl acetate/diisopropyl ether, m.p.=75° C.

I.R. spectrum: 3340 and 3450 cm$^{-1}$ (OH, NH stretching), 1690–1700 cm$^{-1}$ (broad band: C=O amide).

In a similar manner it has been prepared the 1,3-dihydroxy-1-(4-methylsulfonyl-phenyl)-2-ethoxycarbonylamino-propane which, after crystallization from ethyl acetate, showed (IR analysis) the following peaks: 3200–3360 cm$^{-1}$ (broad band—OH and NH stretching), 1715 cm$^{-1}$ (CO amide).

EXAMPLE 7

Cyclization of compound (F) to 5-(4-methylthio-phenyl)-4-hydroxy-oxazolidin-2-one (G)

Compound (F) (5 g; 17.5 mmols) has been dissolved in warm toluene (25 ml). To this solution, an equimolar amount of potassium ter.butyrate has been added and the reaction mixture has been refluxed for 3 hours. Afterwards, almost all the solvent has been evaporated; water and ice have been added to the residue and the precipitate has been collected by filtration. The thus obtained crude (G) has been recrystallized from ethanol (3.7 g; yield, 88%); m.p. 130°–131° C.

I.R. Spectrum: 3180, 3240, 3300 cm$^{-1}$ (OH and NH stretching) 1720; 1745 cm$^{-1}$ (C=O, oxazolidinone);

NMR in DMSO, delta: 7,64 and 8,0, two doublets, 2H each one of p-substituted phenyl; 7.88, S, 1H, NH amido; 5.48, d, 1H, benzyl, hydrogen; 3.56, m, 2H, hydroxymethyl; 5.16, m, H linked to C4 of oxazolidinone ring; 3.2, S, 3H, CH$_3$S—.

EXAMPLE 8

Oxidation of compound (G) to 5-(4-methylsulfonyl-phenyl)-4-hydroxymethyl-oxazolidin-2-one (H)

Compound (G) (53 g; 221 mmols) has been added portionwise to 84 ml of hydrogen peroxide (10 vol.) maintained under stirring at 40°–45° C. After completion of the addition, the stirring has been continued for further 20 hours at 40° C.

Acetic anhydride (76.6 g; 20.7 ml) has been dropped into the reaction mixture by keeping the temperature below 40° C.

The reaction mixture has been then cooled to 20°–22° C. and maintained under stirring at this temperature for 3 hours and, finally, allowed to stand in refrigerator overnight.

Afterwards, the solvent has been evaporated with caution in vacuo at 40° C.; hot ethanol has been added to the thus obtained residue. The solvent has been again evaporated and the residue crysallized from methyl alcohol. 48.6 g of product (H) yield, 81%. m.p. 172°–174° C.

I.R. spectrum: 1710 cm$^{-1}$ (C=O, amide) 3470, 3340, 3250, 3200 cm$^{-1}$ (OH and NH).

EXAMPLE 9

Preparation of 5-(4-methylsulfonyl-phenyl)-4-methanesulfonylxoymethyl-oxazolidin-2-one (J) from (H)

Compound (H) (200 mg; 0.84 mmols) has been dissolved in anhydrous pyridine (3 ml). The thus obtained solution has been cooled to 0° C. and added with freshly distilled methanesulfonyl chloride (0.06 ml). The solution has been maintained at 0° C. overnight and then diluted with an aqueous solution of hydrochloric acid (stoichiometric amount with respect to pyridine) and ice. After extraction with ethyl acetate, the organic extract has been dried over sodium sulfate and evaporated in vacuo to afford crude (J); yield, 85–90%.

I.R. spectrum: 3300 cm$^{-1}$ (NH), 1760 and 1740 cm$^{-1}$.

When treated according to the techniques described in Examples 15 and 18, compound (H) affords 5-(4-methylsulfonyl-phenyl)-4-fluoromethyl-oxazolidin-2-one which can be then processed according to usual methods to give D-threo-1-(4-methylsulfonyl-phenyl)-1-hydroxy-2-trifluoroacetamido-3-fluoro-propane.

EXAMPLE 10

Preparation of D(—)-threo-2-phenyl-4-hydroxymethyl-5-(4-methylthiophenyl)-2-oxazoline (K)

(i) D-(—)-threo-1-(4-methylthiophenyl)-2-amino-1,3-propanediol (20 g; 94 mmols) has been thoroughly mixed with benzamidine hydrochloride dihydrate (25 g; 130 mmols) and melted at 100° C. The melted mass, after 1 hour at said temperature has been cooled.

To the cooled mass has been added ethyl alcohol (850 ml) and the mixture has been refluxed till complete dissolution. The solution has been then filtered with active carbon and cooled to −10° C. The crystalline precipitate has been collected by filtration and dried at 50° C. under reduced pressure for 10 hours.

19 g (69%) of compound (K) have been thus obtained, m.p. 174°–176° C.

The thus obtained product has been purified by crystallization from ethyl alcohol (400 ml), filtered and dried at 60° C. under reduced pressure for 8 hours.

Yield, 17 g (62%); m.p. 175°–177° C.

(ii) A solution of 390.6 g (1.83 moles) of D-(—)-threo-1-(4-methylthiophenyl)-2-amino-1,3-propanediol and 374 g (2.01 moles) of ethyl benzimidate hydrochloride in 500 ml of water was warmed under stirring at 30° C. for 20 hours.

The mixture was cooled at 5° C. and the resulting precipitate was filtered, washed with water and dried in vacuum at 50° C.

The crude oxazoline was purified by recrystallization from ethanol to give 395 g (72%) of product (K), m.p. 172°–73°0 C.

The following compounds can be prepared in a similar manner from D-(—)-threo-1-(4-methylthiophenyl)-2-amino-1,3-propanediol and the proper imidate:

D-(—)-threo-2-(4-nitrophenyl)-4-hydroxymethyl-5-(4-methylthiophenyl)-2-oxazoline, D-(—)-threo-2-benzyl-4-hydroxymethyl-5-(4-methylthiophenyl)-2-oxazoline.

EXAMPLE 11

Preparation of D-(—)threo-2-methyl-4-hydroxymethyl-5-(4-methylthiophenyl)-2-oxazoline (L)

Ethyl acetoimidate hydrochloride (50 g; 400 mmols) has been suspended in dichloromethane (360 ml). To the thus obtained suspension has been added D-(—)-threo-1-(4-methylthiophenyl)-2-amino-1,3-propanediol (76.37 g; 358 mmols). The reaction mixture has been stirred for 5 hours and then poured into ice and water (230 g).

The aqueous layer has been separated and extracted with dichloromethane (60 ml). The combined organic extracts has been washed with water, dried on sodium sulfate and evaporated to dryness.

Crystalline product (L) (69.50 g; 81%) has been thus obtained which has been purified by crystallization from methyl-ter.butyl-ether (1750 ml), filtration and drying in vacuo at 40°–50° C. Yield, 55.60 g (65%) m.p. 111°–113° C.

In a similar manner has been prepared D-(−)-threo-2-methyl-4-hydroxymethyl-5-(4-methylsulfonylphenyl)-2-oxazoline melting at 153°–155° C.

EXAMPLE 12

Preparation of D-(−)-threo-2-phenyl-4-hydroxymethyl-5-(-methylsulfonylphenyl)-2-oxazoline (M)

D-(−)-threo-2-phenyl-4-hydroxymethyl-5-(4-methylthiophenyl)-2-oxazoline (5 g; 16.7 mmols) prepared as disclosed by Example 10 above, has been added portionwise to acetic anhydride (5.80 ml) under stirring at 35° C. Into the thus obtained suspension, has been dropped hydrogen peroxide (20 ml; 130 volumes) maintaining the temperature at 35°–40° C. external cooling.

After completion of the addition, stirring has been continued at 35° C. till complete dissolution and the solution is allowed to stand overnight at 4° C. To the reaction mixture has been added water (25 ml). The precipitate has been separated by filtration, washed on the filter till neutral and then dried in vacuo at 60° C. to afford 4.4 g of the desired product (M) which has been purified by crystallization from methyl alcohol (400 ml). Yield, 3.80 g (68.5%); m.p. 209°–211° C.

EXAMPLE 13

Preparation of D-(−)threo-2-dichloromethyl-4-methanesulfonyloxymethyl-5-(4-methylsulfonylphenyl)-2-oxazoline (N)

Methanesulfonyl chloride (8.13 ml; 105 mmols) has been dropped in 15 minutes into a solution of D-(−)-threo-1-(4-methylsulfonylphenyl)-2-dichloroacetylamino-1,3-propane diol (35.60 g; 100 mmols) in anhydrous pyridine (136 ml) maintained under stirring at 0° C.

The reaction mixture has been kept under stirring for 1 further hour and then allowed to stand in refrigerator overnight.

The thus obtained mixture has been poured into a mixture of concentrated hydrochloric acid (150 ml) and ice and extracted with ethyl acetate (500 ml×2).

The combined organic extracts has been washed with 5% hydrochloric acid (200 ml) and then with water till neutral, dried over sodium sulfate and evaporated to dryness.

The residue has been purified by crystallization from ethyl alcohol (200 ml).

24.4 g (56%) of D-(−)-threo-1-(4-methylsulfonylphenyl)-2-dichloroacetylamino-3-methanesulfonyloxypropanol melting at 109°–112° C. have been thus obtained.

A mixture of this product (2 g; 4.6 mmols) and of methanesulfonic acid (0.) in 35 ml of 1,2-dichloroethane, has been refluxed in a round-bottomed flask equipped with a water trap for 3 hrs. The reaction mixture has been cooled and washed with water.

The organic layer has been separated, dried over sodium sulfate and evaporated to dryness. The residue (0.7 g) has been purified by chromatography on a silica gel column (70 g) eluting with dichloromethane/methyl alcohol (9.5:0.5). The fraction containing the desired product (N) has been isolated and evaporate to dryness.

It has been thus obtained a product (200 mg) melting at 116°–118° C. which show a NMR spectrum consistent with the structural formula.

In a similar manner may be prepared from D-threo-(1-(4-methylsulfonylphenyl)-2-trifluoroacetylamino-1,3-propanediol (British Patent No. 1534387) the correspondent D-(threo-(−)-2-trifluoromethyl-4-hydroxymethyl-5-(4-methylsulfonylphenyl)-2-oxazoline.

EXAMPLE 14

Preparation of D-(−)-threo-2-phenyl-4-methanesulfonyloxymethyl-5-(4-methylthiophenyl)-2-oxazoline (O)

A mixture of product (K) (4 g; 13.37 mmols) prepared as disclosed in Example 10 above, in anhydrous pyridine (15 ml) has been kept under stirring at room temperature for about 1 hr. After cooling to 0° C. has been added dropwise methane sulfonyl chloride (1145 ml; 14.7 mmols) and stirring has been continued for 2 further hrs maintaining the temperature at 0° C. The mixture has been then allowed to stand at about 3° C. for 3 hrs. Ice has been added to the reaction mixture and the thus obtained solid has been filtered and dried in vacuo at room temperature.

4.96 g of chromatographically (T.L.C.) pure product (O) have been thus obtained.

Yield, 98%; m.p. 107°–108°.

The following compounds can be prepared in a similar manner:

D-(−)-threo-2-methyl-4-methanesulfonyloxymethyl-5-(4-methylthiophenyl)-2-oxazoline, D-(−)-threo-2-benzyl-4-methanesulfonyloxymethyl-5-(4-methylthiophenyl)-2-oxazoline, D-(−)-threo-2-trifluoromethyl-4-methanesulfonyloxymethyl-5-(4-methylsulfonylhenyl)-2-oxazoline, D-(−)-threo-2-(4-nitrophenyl)-4-methanesulfonyloxymethyl-5-(4-methylthiophenyl-2-oxazoline.

EXAMPLE 15

Preparation of D-(−)-threo-2-phenyl-4-fluoromethyl-5-(4-methylthiophenyl)-2-oxazoline (P)

Product (O) (4 g; 10.61 mmols) prepared as disclosed in Example 14 and anhydrous potassium fluoride (6.164 g; 106 mmols) in polyethylene glycol 400 (25 ml) have been maintained under stirring at 100°–105° C. for 19 hours. After having added water, the mixture has been extracted with ethyl ether (3×10 ml). The combined organic extracts have been dried over sodium sulfate and evaporated to dryness. The oily residue has been purified by flash chromatography on a silica gel column eluting at first with 900 ml of ethyl acetate/petroleum ether 1:9 and then with 1500 ml of ethyl acetate/petroleum ether 2:8.

2.19 g (Yield, 68.5%) of product (O) have been thus obtained.

An analytically pure sample has been prepared by crystallization from isopropanol; m.p. 70°–72° C.

N.M.R. (CDCl$_3$) delta: 5.5 d, (J=7 Hz) (H—C5); 5.08, d.d, (1H) (CH$_2$F); 4.13–4.71, m, 2H (H—C4 and —CH$_2$F).

The following compunds can be prepared in a similar manner:

D-(−)-threo-2-methyl-4-fluoromethyl-5-(4-methyl-thiophenyl)-oxazoline,

D-(−)-threo-2-benzyl-4-fluoromethyl-5-(4-methylthiophenyl)-oxazoline,

D-(−)-threo-2-trifluoromethyl-4-fluoromethyl-5-(4-methylthiophenyl)-2-oxazoline, D-(−)-threo-(4-nitrophenyl)-4-fluoromethyl-5-(4-methylthiophenyl)-2-oxazoline.

EXAMPLE 16

Preparation of
D-(—)-threo-1-(4-methylthiophenyl)-2-amino-3-fluoro-1-propanol (Q)

Product (P) (1.01 g; 3.35 mmols) prepared as disclosed in Example 15 has been added to 2N hydrochloric acid (18 ml) and maintained under stirring at 100°–105° C. After 50 minutes, further 20 ml of 2N hydrochloric acid have been added and the stirring is continued at 100°–105° C. After 3 hrs and a half the solution has been cooled and extracted with ethyl ether (20 ml×2). The aqueous layer has been at first made basic with sodium bicarbonate and the satured with potassium carbonate. Finally it has been extracted with chloroform (20 ml×3). The combined organic extracts have been evaporated to dryness in vacuo.

0.64 g of product (Q) have been thus obtained. Yield, 88%.

Compound (Q) can be reacted with the desired haloacetic acid as disclosed in Example 5 to afford
D-(—)-threo-1-(4-methylthiophenyl)-1-hydroxy-2-dichloroacetamido-3-fluoro-propane,
D-(—)-threo-1-(4-methylthiophenyl)-1-hydroxy-2-trifluoroacetamido-3-fluoro-propane.

EXAMPLE 17

Preparation of
D-(—)-threo-2-phenyl-4-methanesulfonyloxymethyl-5-(4-methylsulfonylphenyl)-2-oxazoline (R)

To a mixture of product (M) (0.3 g; 0.9 mmols) prepared as disclosed in Example 12, in pyridine (5 ml) has been added methanesulfonyl chloride (0.077 ml; 0.99 mmols) at 0° C.

After having continued the stirring at 0° C. for 10 minutes, the mixture has been allowed to stand in refrigerator overnight. The mixture has been then made acid, extracted with ethyl acetate (15 ml×2), dried over sodium sulfate and evaporated to dryness in vacuo.

0.32 g of product (R) have been thus obtained. Yield, 87%.

EXAMPLE 18

Preparation of
D-(—)-threo-2-phenyl-4-fluoromethyl-5-(4-methylsulfonylphenyl)-2-oxazoline (S)

Product (R) (0.32 g; 0.78 mmols) prepared as disclosed in Example 17 above and anhydrous potassium fluoride (0.53 g; 0.91 mmols) in polyethylene glycol (400 ml) have been kept under stirring at 90°–95° C. for 3 hrs, then at 75° C. for 17 hrs and, finally, at 110° C. for 6 hrs. The reaction mixture has been worked up as disclosed in Example 15 and have been thus obtained 0.13 g of product (S). Yield, 50%

N.M.R. (CDCl$_3$) delta: 5.76 d, (J=7 Hz, H—C); 5.16, d.d, (1H) (—CH$_2$F); 4.2–4.75, m, (2H), (H—C4 and —CH$_2$F).

Compound (S) can be reacted with hydrochloric acid in a manner similar to that disclosed in Example 16 to give D-(—)-threo-1-(4-methylsulfonylphenyl)-2-amino-3-fluoro-1-propanol which is then reacted with the desired haloacetic acid in a manner similar to that disclosed in Example 5 to afford D-threo-1-(4-methylsulfonylphenyl)-1-hydroxy-2-dichloroacetamido-3-fluoropropane, D-threo-1-(4-methylsulfonylphenyl)-1-hydroxy-2-trifluoroacetamido-3-fluoro-propane.

We claim:
1. A process for preparing a compound of formula

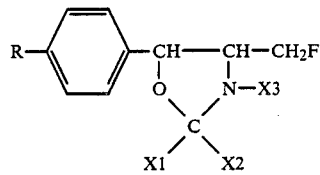

(III)

wherein

R is a methylthio, methylsulfoxy, methylsulfonyl or nitro group; and

X1 is hydrogen, 1–6 carbon alkyl, 1–6 carbon haloalkyl, 3–6 carbon cycloalkyl, phenyl or 1–6 carbon phenylalkyl, which phenyl ring may be substituted by one or two halogen atoms, 1–3 carbon alkyl, 1–3 carbon alkoxy or nitro groups; or X1 together with X2 is an oxygen atom or an alkylene having from 2–5 carbon atoms; and X2 is hydrogen, 1–6 carbon alkyl, 1–6 carbon haloalkyl, 3–6 carbon cycloalkyl or phenyl which may be substituted by one or two halogen atoms, 1–3 carbon alkyl, 1–3 carbon alkoxy or nitro groups; or X2 together with X1 is an oxygen atom or an alkylene having from 2–5 carbon atoms; or X2 is covalently linked to X3; and X3 is hydrogen or —CO—R4 wherein R4 is hydrogen, 1–6 carbon alkyl, 1–6 carbon haloalkyl, 3–6 carbon cycloalkyl, phenyl or 1–6 carbon phenylalkyl, which phenyl ring may be substituted by one or two halogen atoms, 1–3 carbon alkyl, 1–3 carbon alkoxy or nitro groups; or R4 together with X2 is

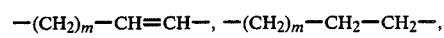

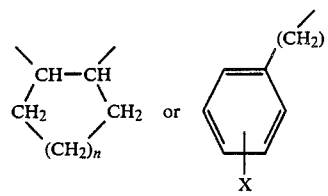

wherein n is 1 or 2; m is 0 or 1; X is hydrogen, a halogen atom, 1–3 carbon alkyl, 1–3 carbon alkoxy or nitro groups; or R4 together with X2 and X1 is a chain of formula

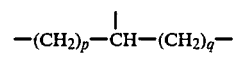

where p is 3 or 4 and q is 1 or 2; or

X3 is covalently linked with X2;

which process comprises reacting one mole of a compound of formula

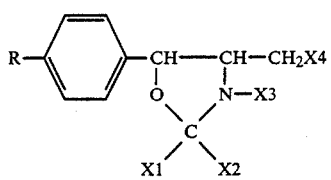

wherein

R, X1, X2 and X3 are as is defined above, and wherein

X4 is —O—SO$_2$R6 wherein R6 is methyl, trifluoromethyl, phenyl, p-methyl-phenyl, 2,4,6-trimethylphenyl, 2-naphthyl or 2-pyridyl with from 1 to 15 moles of a non gaseous inorganic fluoride in a polyglycol having at least 4 alkylidene oxide units at a temperature of from 40° to 150° C. and retaining said compound of formula III formed in the reaction mixture until completion of the reaction.

2. A process according to claim 1, wherein said inorganic fluoride is selected from the group consisting of alkali metal, alkaline-earth metal, ammonium and phosphonium fluorides.

3. A process according to claim 1, wherein said inorganic fluoride is sodium fluoride or potassium fluoride.

4. A process according to claim 1, wherein said polyglycol is represented by the formula HO—(AO)$_s$—H wherein A is a straight or branched alkylidene having from 2 to 6 carbon atoms, and s is an integer ranging from 4 to 50.

5. A process according to claim 2, wherein said polyglycol is represented by the formula HO—(AO)$_s$—H wherein A is a straight or branched alkylidene having from 2 to 6 carbon atoms, and s is an integer ranging from 4 to 50.

6. A process according to claim 3, wherein the polyglycol is represented by the formula HO—(AO)$_s$—H wherein A is a straight or branched alkylidene having from 2 to 6 carbon atoms, and s is an integer ranging from 4 to 50.

7. A process according to claim 4, wherein said polyglycol is a polyethylene glycol.

8. A process according to claim 5, wherein said polyglycol is a polyethylene glycol.

9. A process according to claim 6, wherein said polyglycol is a polyethylene glycol.

* * * * *